United States Patent [19]
Marino

[11] Patent Number: 6,030,401
[45] Date of Patent: Feb. 29, 2000

[54] VERTEBRAL ENPLATE DECORTICATOR AND OSTEOPHYTE RESECTOR

[75] Inventor: James F. Marino, La Jolla, Calif.

[73] Assignee: NuVasive, Inc., San Diego, Calif.

[21] Appl. No.: 09/168,306

[22] Filed: Oct. 7, 1998

[51] Int. Cl.[7] .................................................. A61B 17/14
[52] U.S. Cl. .......................................... 606/180; 606/170
[58] Field of Search .................................. 606/170, 180, 606/83; D08/62, 90

[56] References Cited

U.S. PATENT DOCUMENTS

| | | |
|---|---|---|
| 4,844,088 | 7/1989 | Kambin . |
| 5,062,845 | 11/1991 | Kuslich et al. ............................ 606/80 |
| 5,285,795 | 2/1994 | Ryan et al. .............................. 128/750 |
| 5,383,884 | 1/1995 | Summers ................................. 606/170 |
| 5,423,844 | 6/1995 | Miller ...................................... 606/171 |
| 5,437,630 | 8/1995 | Daniel et al. .............................. 604/22 |
| 5,489,291 | 2/1996 | Wiley ....................................... 606/170 |
| 5,527,331 | 6/1996 | Kresch et al. ........................... 606/170 |
| 5,569,284 | 10/1996 | Young et al. ............................ 606/180 |
| 5,618,293 | 4/1997 | Sample et al. .......................... 606/170 |
| 5,630,826 | 5/1997 | Sastri ....................................... 606/170 |
| 5,669,926 | 9/1997 | Aust et al. ............................... 606/170 |

Primary Examiner—Michael Buiz
Assistant Examiner—Julian W. Woo
Attorney, Agent, or Firm—Townsend Townsend & Crew LLP

[57] ABSTRACT

A device for removing cortical tissue from a vertebral endplate, comprising: an elongated handle; a rotatably-mounted driving rod received in said handle; a dumbbell-shaped burr connected to said driving rod; and an eccentric support having first and second opposite ends, said first end being connected to said handle and said second forming a collar around said dumbbell-shaped burr.

10 Claims, 11 Drawing Sheets

VERTEBRAL ENPLATE DECORTICATOR AND OSTEOPHYTE RESECTOR

TECHNICAL FIELD

The present invention relates to devices used for minimally invasive spinal surgery and more particularly to devices used for endplate decortication and for osteophyte resection during minimally invasive surgery.

BACKGROUND OF THE INVENTION

When performing spinal surgery such as when inserting interbody fusion devices between adjacent vertebrae, the endplates of the adjacent vertebrae are first preferably decorticated to encourage the growth of bone and cause bone fusion by exposing cancellous bone. Additionally, osteophytes projecting outwardly from the sides of the vertebrae should be removed during surgery as they may damage nerves or other soft tissues.

Typically, curettes, scrapers or other filing instruments are used for osteophyte resection and chisels or drills are used for removing bone cortical tissue. It is not possible to leverage conventional curettes or scrapers against the vertebrae while operating these devices since these devices must move freely back and forth against the osteophyte to wear it down. Conventional decortication systems are also limited. In particular, when decorticating with a chisel or drill, substantially all of the cortical tissue is typically removed during the procedure. It would instead be preferable to provide decortication in the form of deep scratches on the vertebral endplates, thereby not removing all cortical tissue. An advantage of not removing all cortical tissue is that the vertebrae will retain sufficient structural support to hold an intervertebral insert firmly in position.

During minimally invasive spinal surgery, access to a patient's intervertebral space can be provided through a cannulated percutaneous posterolateral approach. An example of such minimally invasive surgery is described in the Applicant's provisionally filed patent application entitled "Minimally Invasive Spinal Surgery Systems", filed Jun. 9th, 1998, (Attorney Docket No. 18608-000600), incorporated herein by reference in its entirety.

Unfortunately, a disadvantage of present endplate decorticators and osteophyte resectors is the difficulty of firmly holding these devices against the vertebral surface being resected or decorticated during operation. As such devices can not be firmly leveraged against vertebral bones, the abrasion effectiveness of existing devices is somewhat limited. This disadvantage of existing endplate decorticators and osteophyte resectors is especially pronounced in the area of minimally invasive surgery. In particular, due to their large and bulky size, existing endplate decorticators and osteophyte resectors are not adapted to be received through percutaneously inserted cannulae into the patient's intervertebral space. Rather, existing decorticators and resectors are typically dimensioned such that they can only be used during highly invasive surgical procedures, such as when access to the patient's intervertebral space is accomplished by open spinal surgery.

An additional disadvantage of existing endplate decorticators and osteophyte resectors is that these exist as two very different devices. It would instead be desirable to provide a single device offering the combined benefits of endplate decorticators and osteophyte resectors.

SUMMARY OF THE INVENTION

The present invention provides an instrument which can be used as a vertebral endplate decorticator and/or as an osteophyte resector and is preferably dimensioned to be received through a percutaneously inserted cannula into a patient's back. When used as either an endplate decorticator or as an osteophyte resector, the present invention includes a eccentric support structure projecting laterally from the instrument and having a surface for contacting vertebral bone with a stationary surface during use, and wherein the eccentric support can be leveraged or pivoted against vertebral bone structures, thereby enhancing its resection or decortication effect, while being firmly locked into position during operation. As such, the present device is adapted to be easily locked into position without interfering with resection or decortication. The present instrument can be easily manipulated within the cannula so that it can be held tightly in place against one or the other of two adjacent vertebrae, thereby positioning it to decorticate or resect the opposite vertebra, as desired.

In preferred embodiments, the present instrument comprises a rotatable burr connected to a distal end of rotatable driving rod. An elongated handle surrounds the driving rod and the eccentric support projects radially outward from the end of the handle proximal the rotatable burr. In preferred embodiments, the eccentric support projects outwardly to a distance greater than the radius of the rotating burr and is disposed on one side of the burr.

In one specific preferred embodiment, the burr is dumbbell-shaped and is supported by a collar which is disposed around the narrow center portion of the dumbbell-shaped burr. The collar is preferably integrally formed together with the eccentric support. The collar provides support to the burr, (while minimizing torque on the driving rod), such that the burr can be held firmly against a vertebral surface, thereby increasing decortication or resection effectiveness. A tab or other structure projects radially outwardly from the collar, between the two lobes of the dumbbell burr, to provide the support surface for engaging bone and providing the desired pivot point. The tab will also preferably be formed integrally with the elongated handle.

Accordingly, the handle defines the axis about which the burr rotates and the eccentric support operates as a fulcrum which is spaced apart from, and preferably opposite to, the contact area between the rotating burr and the bone.

In another preferred embodiment, the burr is generally cylindrical in shape. An advantage of such a cylindrically-shaped burr is its large abrasive surface.

An advantage of the present instrument is that by rotating its handle, the eccentric support can be wedged against a first vertebra such that the rotating burr is held tightly against an adjacent second vertebra, thus producing an effective system for decorticating or resecting the surface of the second vertebra. Preferably as well, the eccentric support may have one or more teeth or other similar gripping structures thereon to assist in firmly holding the instrument against the first vertebral surface while operating on the second vertebral surface. By rotating the handle to firmly wedging the gripping teeth of the eccentric support into the first vertebrae, the present instrument is prevented from slipping across the vertebral surface being decorticated or resected while the burr is being rotated.

DESCRIPTION OF THE PREFERRED EMBODIMENT

Figure 1:
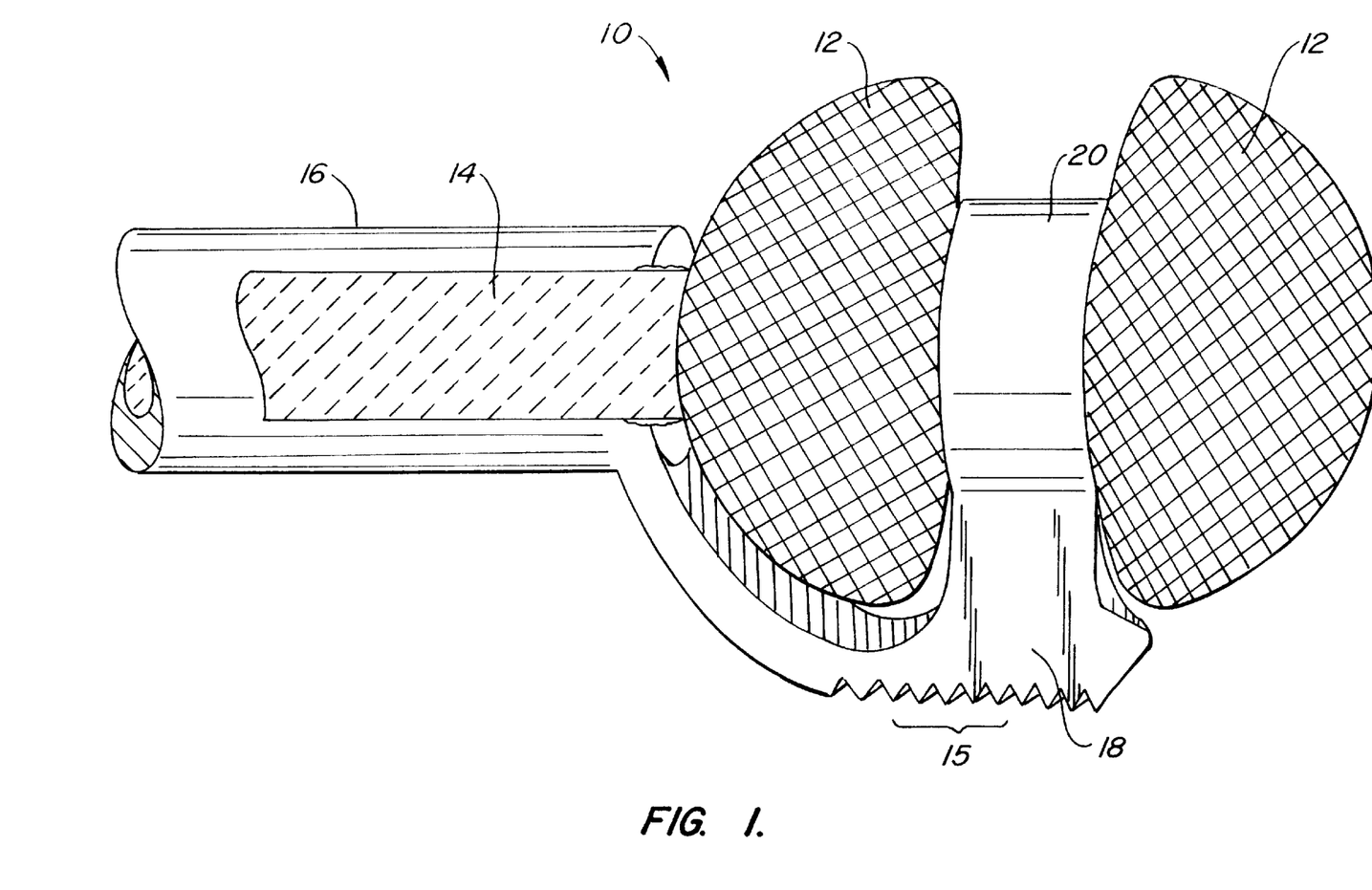
FIG. 1 is a side perspective view of a first embodiment of the present instrument.

FIG. 1 shows a side perspective view of a first embodiment of the present invention. Specifically, instrument 10 comprises a dumbbell-shaped burr 12 which is axially connected to driving rod 14. Rotation of driving rod 14 causes rotation of burr 12, thereby providing effective endplate decortication when burr 12 is held against a vertebral endplate, as will be explained.

Driving rod 14 is mounted to be freely rotatable within an elongated handle 16. Handle 16 is connected to, or is preferably integrally formed together with, eccentric support 18. Eccentric support 18 is connected to, or is preferably integrally formed together with, collar 20 which supports dumbbell-shaped burr 12 as shown. A plurality of gripping teeth 15 project from eccentric support 18 as shown.

Figure 2:
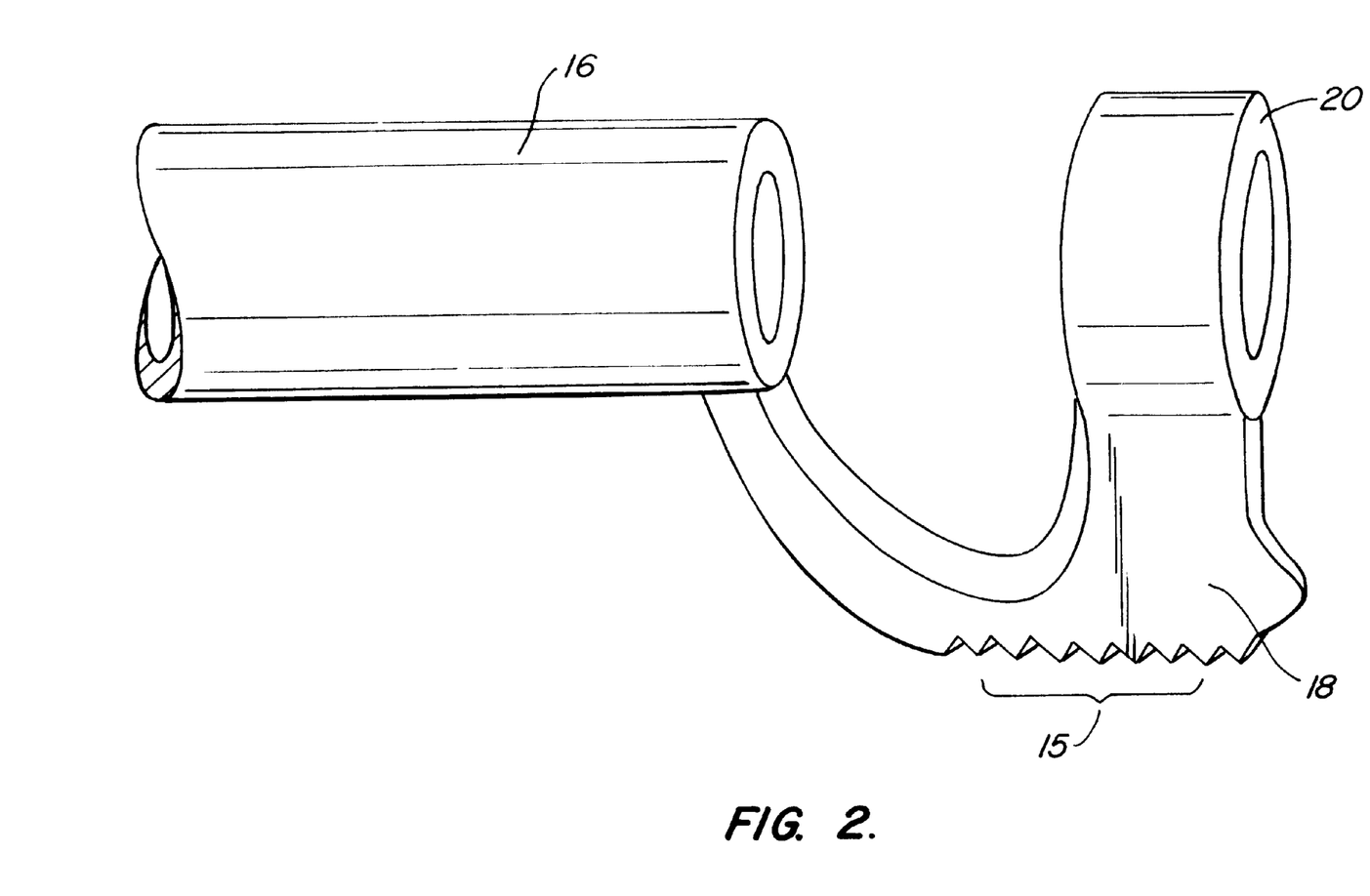
FIG. 2 is a side perspective view of the integrally-formed handle, eccentric support and collar of the instrument of FIG. 1.
Figure 3:
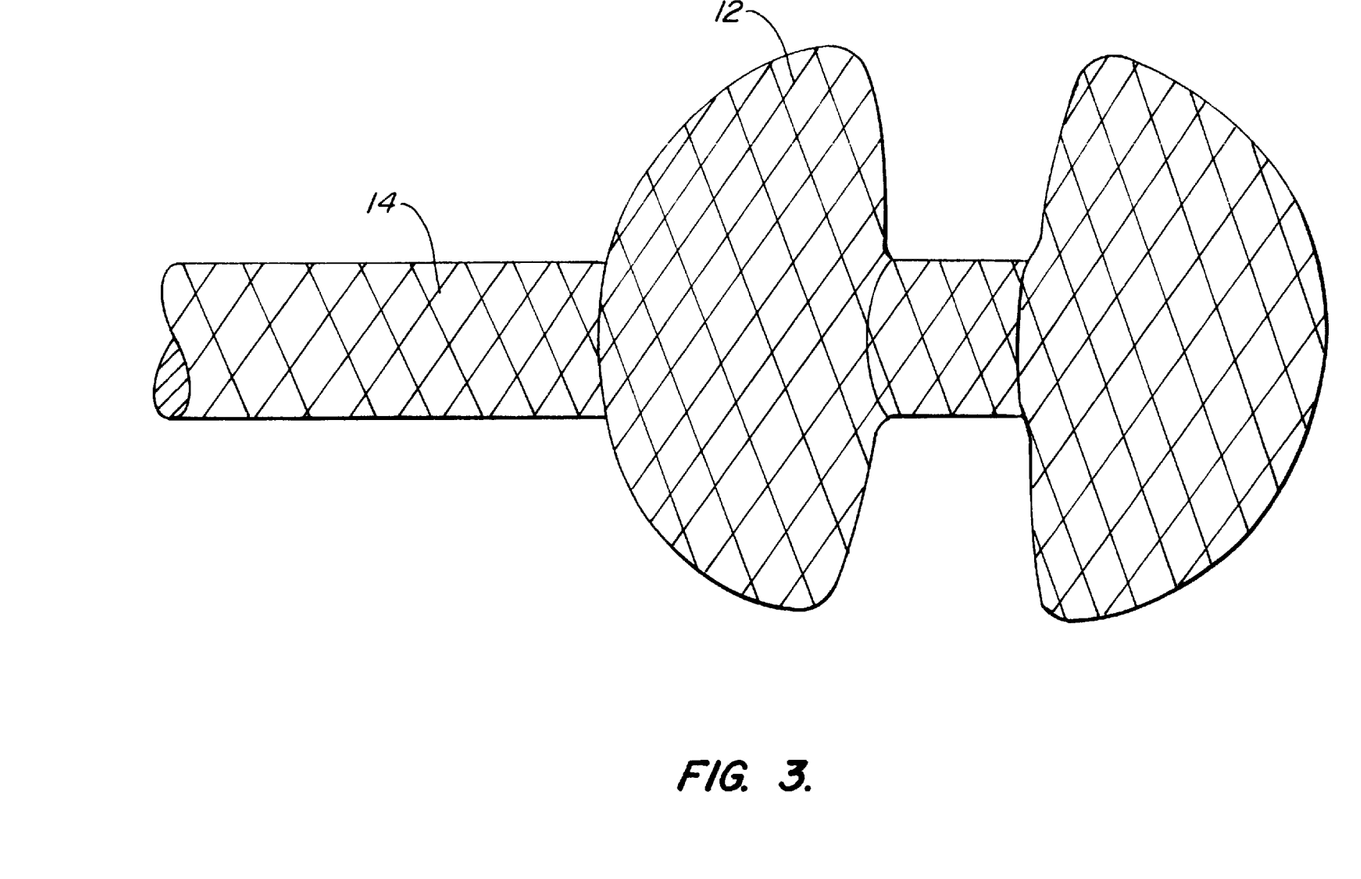
FIG. 3 is a side perspective view of the rotating burr and driving rod of the instrument of FIG. 1.

FIG. 2 shows a side perspective view of handle 16, eccentric support 18, collar 20 and teeth 15 which may preferably be integrally formed together from a single piece of metal such as stainless steel. FIG. 3 shows the burr 12 and attached driving rod 14 as removed from the handle 16, support 18, and collar 20 of FIG. 2. Burr 12 may preferably be formed of carbide steel or stainless steel. Driving rod 14 may preferably be formed of stainless steel.

Rotation of driving rod 14 causes dumbbell-shaped burr 12 attached thereto to simultaneously rotate. The surface of dumbbell-shaped burr 12 is preferably abrasive such that spinning burr 12 can be used to decorticate a vertebral endplate or to resect a vertebral osteophyte. Endplate decortication is useful in promoting bone growth when inserting an intervertebral fusion cage or insert between adjacent vertebrae. Osteophyte resection is useful in preventing damage to nerves or other soft tissues.

Figure 7:
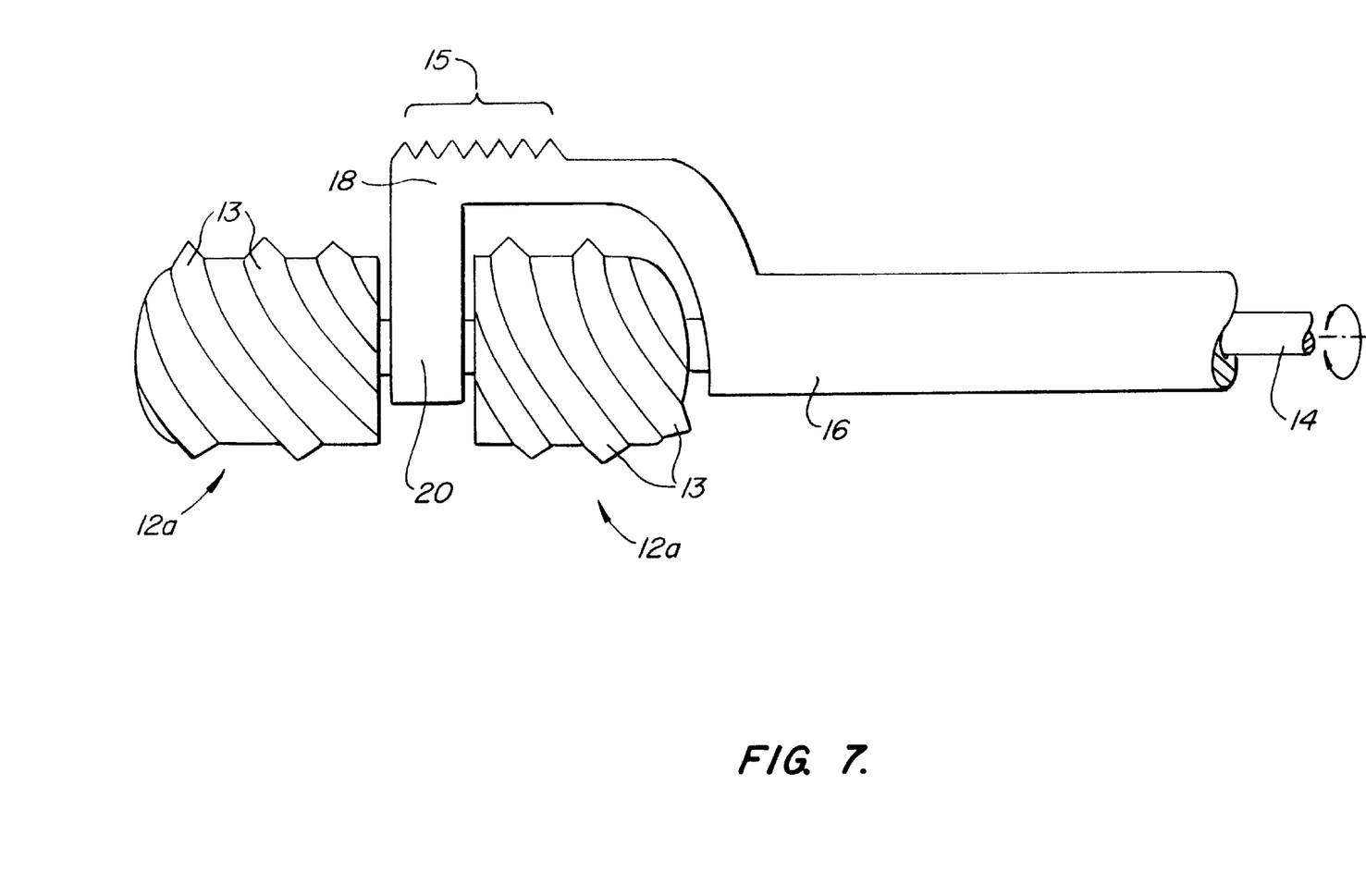
FIG. 7 is a side elevation view of a second embodiment of the present invention.

As shown in FIG. 1, in a preferred aspect of the invention, the surface of spinning burr 12 is a finely abrasive surface is used such that the device is ideally suited for osteophyte resection. Comparatively, as shown in FIG. 7, in an alternate preferred aspect of the invention, the surface of spinning burr 12a is a coarsely abrasive surface is used such that the device is ideally suited for endplate decortication.

Figure 4:
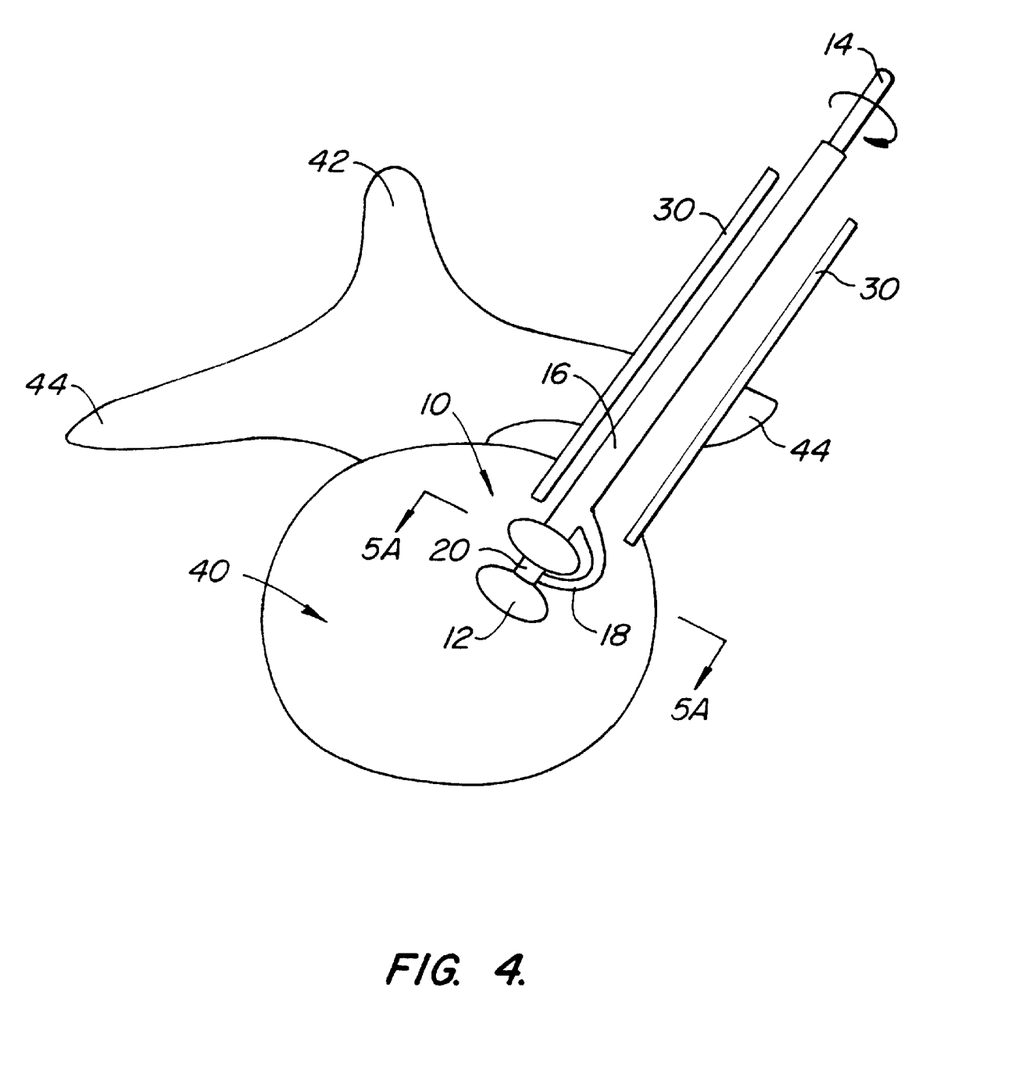
FIG. 4 is a top plan view of the instrument of FIG. 1 as received into a patient's intervertebral space through a posterolaterally inserted cannula.

As can be seen in cross section in FIG. 4, instrument 10 can preferably be received through cannula 30, and positioned in intervertebral space 40, (such as when performing minimally invasive spinal surgery). Most preferably, cannula 30 may be received in a posterolateral approach into the intervertebral space 40, as shown. FIG. 4 further shows the patient's spinous process 42 and transverse processes 44 for perspective.

Figure 5A:
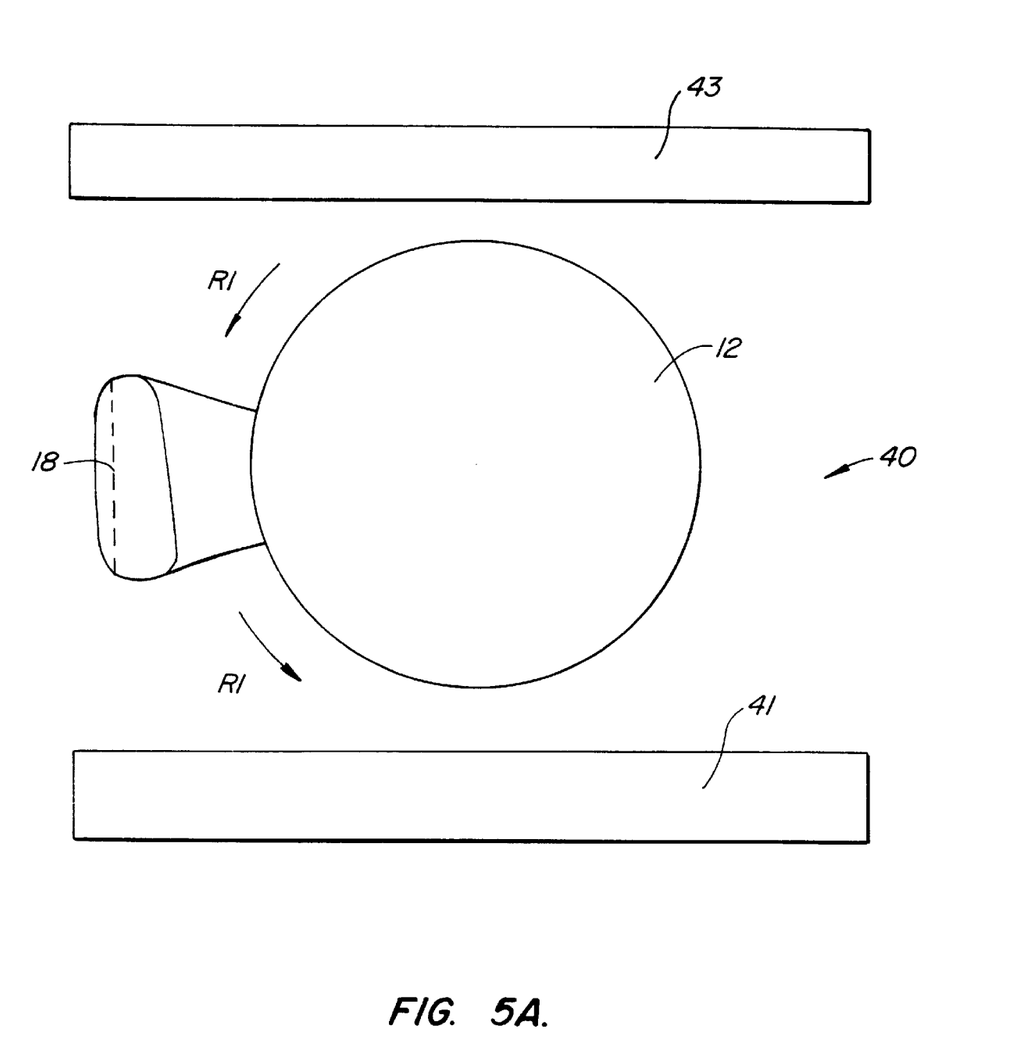
FIG. 5A is an axial sectional view taken along line 5—5 of FIG. 4, with the instrument positioned in a first position between adjacent vertebrae.
Figure 5B:
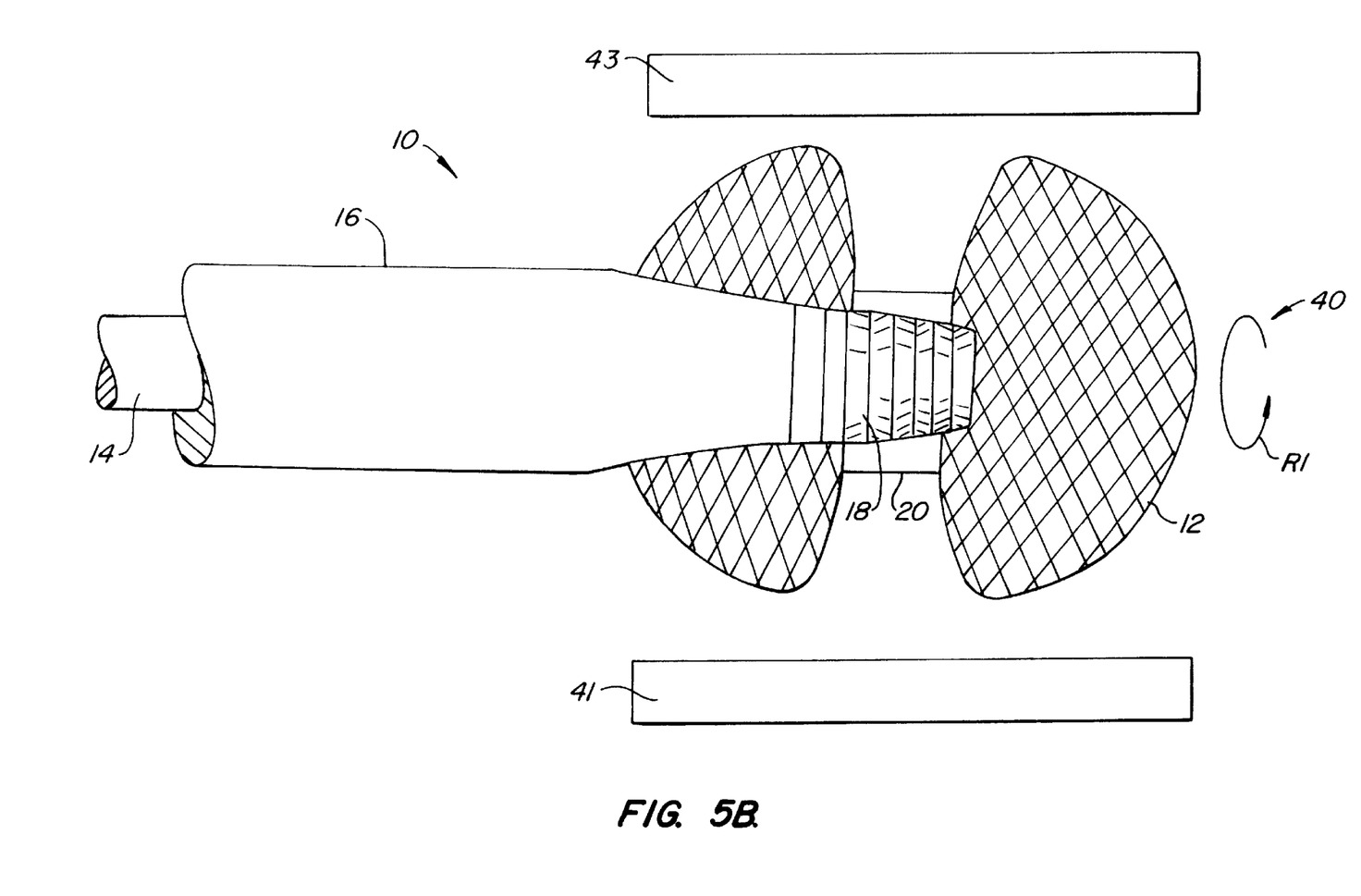
FIG. 5B is a side elevation view corresponding to FIG. 5A.

As can be seen in the axial view of FIG. 5A, (as taken along line 5A—5A in FIG. 4), and in the side view of FIG. 5B, burr 12 is shown as initially positioned in intervertebral space 40 between adjacent vertebrae 41 and 43, positioned therebelow and thereabove respectively. Support 18 is positioned to one side of instrument 10 such that instrument 10 is freely movable in intervertebral space 40 between vertebrae 41 and 43. By subsequently rotating handle 16 in direction R1, support 18 rotates to the position shown in FIGS. 6A and 6B, such that support 18 is thereby pushed firmly against vertebra 41, with teeth 15 projecting into the surface of vertebra 41, as shown. Accordingly, with support 18 being firmly held against vertebra 41, instrument 10 pivots about contact region 19 between support 18 and vertebra 41 such that burr 12 is firmly held in position against vertebrae 43, as shown. With support 18 being wedged against vertebrae 41 in this manner, more abrasive force can be applied to the surface of vertebra 43, (such that it can be decorticated or resected more efficiently), than could be applied in the absence of the pivoting support 18 being wedged against vertebrae 41. Moreover, since support 18 is firmly wedged against vertebrae 41, the likelihood of instrument 10 slipping such that burr 12 shifts position across the surface of vertebra 43 during decortication is substantially reduced. The likelihood of slippage is further reduced by rotating burr 12 in direction R1.

Figure 6A:
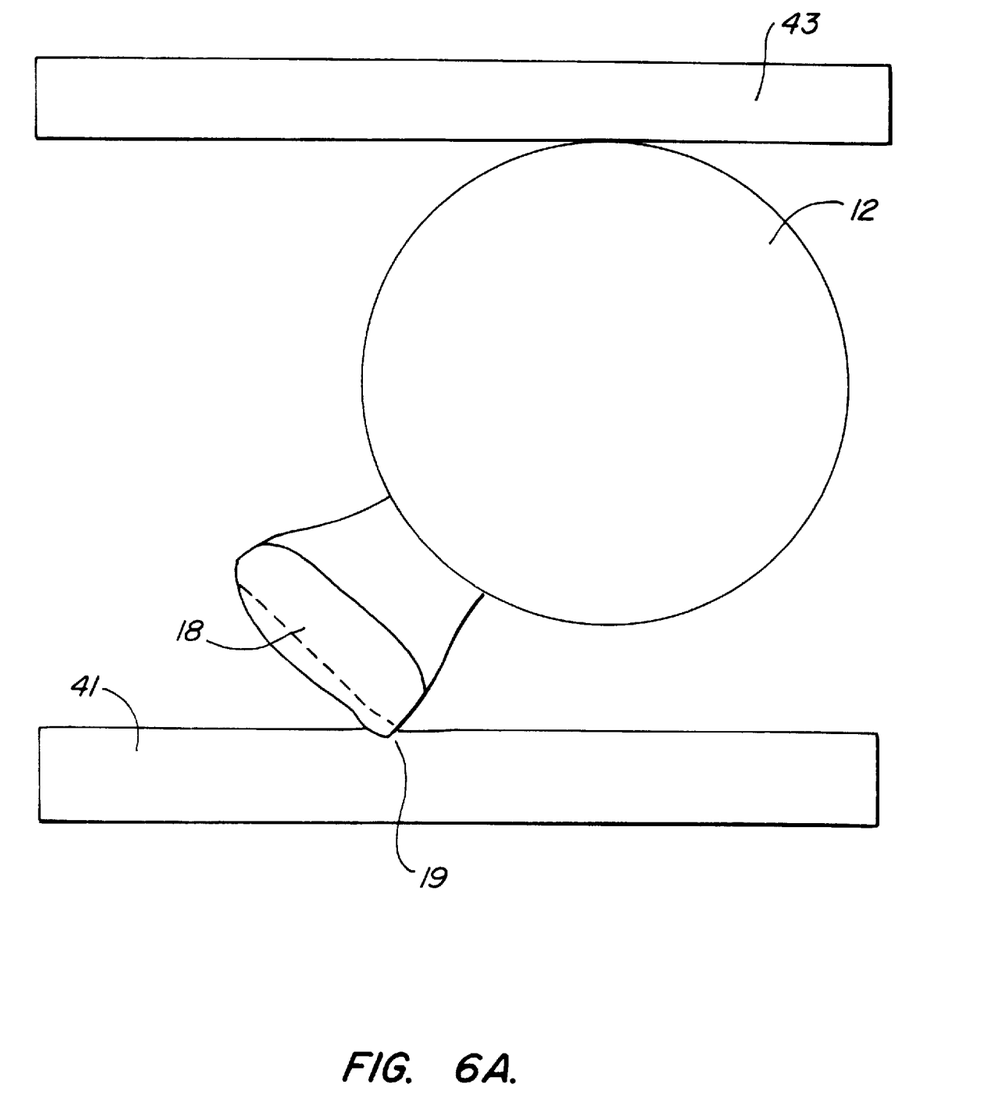
FIG. 6 is a view corresponding to FIG. 4 but with the eccentric support of the instrument rotated to a second position.
Figure 6B:
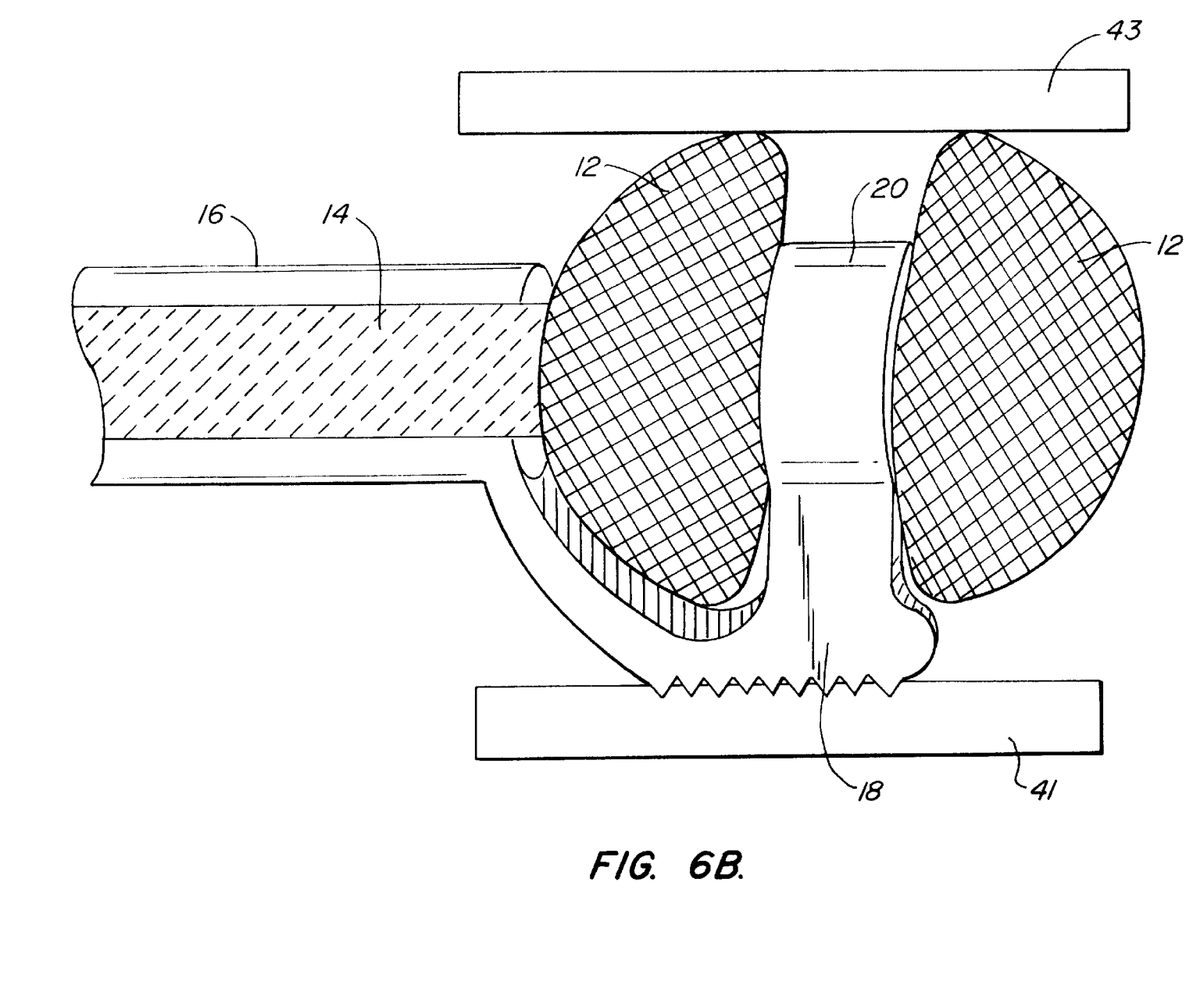
FIG. 6B is a side elevation view corresponding to FIG. 6A.

It is to be appreciated that handle 16 could conversely be rotated in an opposite direction such that support 18 instead rests against vertebrae 43, thereby enabling burr 12 to be forced more firmly against vertebrae 41 while support 18 is anchored in position against the surface of vertebra 43.

In a second embodiment of the present invention, as shown in FIG. 7, rotating burr 12a has spiral cutting teeth 13 disposed thereon. Spiral cutting teeth 13 advantageously increase the abrasion effectiveness of the present invention.

Figure 8:
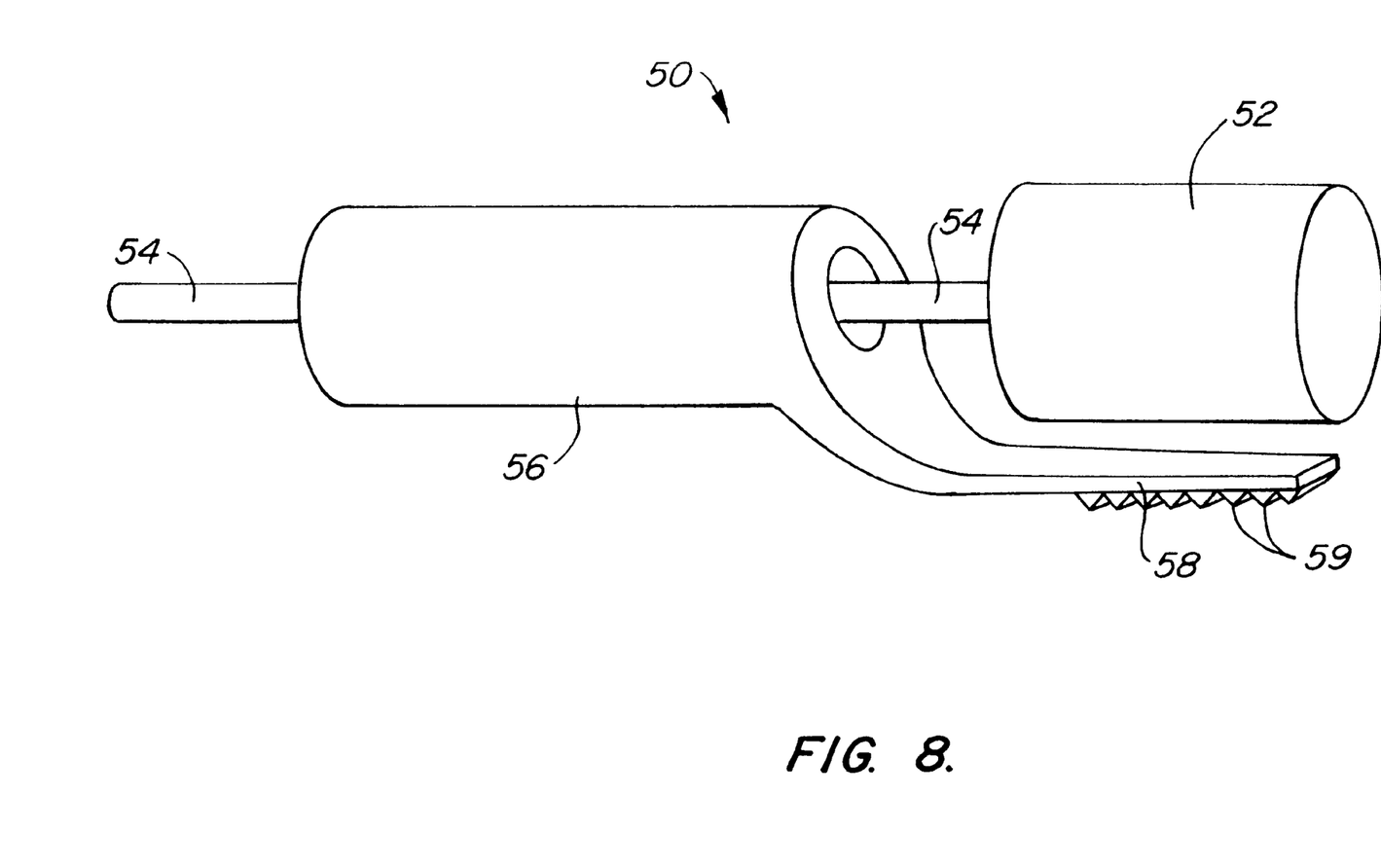
FIG. 8 is a side perspective view of a third embodiment of the present instrument.
Figures 9, 10:
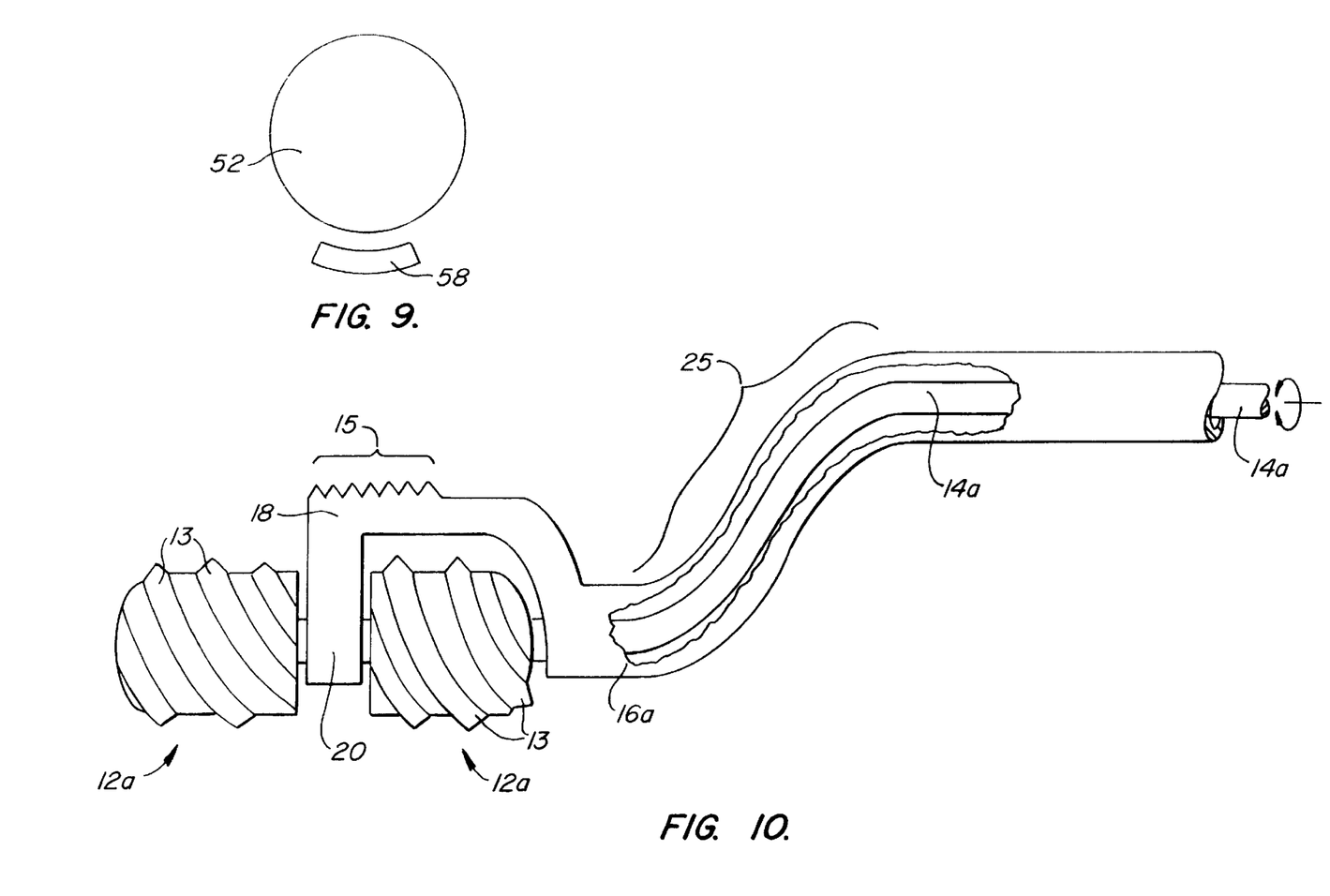
FIG. 9 is an end view of the instrument of FIG. 8.
FIG. 10 is a partially cut away view corresponding to FIG. 7, but with a flexible shaft and driving rod.

In a third embodiment of the present invention, as shown in FIGS. 8 and 9, instrument 50 is provided. A driving rod 54 mounted to rotate freely in handle 56 is provided. A generally cylindrical-shaped burr 52 is axially connected to driving rod 54. An advantage of such a generally cylindrical-shaped burr 52 is its large contact surface when it is held against a vertebral endplate. Handle 56 is preferably formed integral with an eccentric support 58 which projects outwardly beyond the radius of burr 52 as shown. Gripping teeth 59 are also provided. The manner of operation of instrument 50 is substantially identical to that of instrument 10 as set forth above, with handle 56 being rotated such that support 58 rests against a first vertebral surface while burr 52 decorticates or resects a second opposite vertebral surface.

Modification and variation to the present invention can be accomplished without departing from the present invention as described and claimed. For example, as seen in FIG. 10, driving rod 14a can be flexible and be housed within a flexible shaft 16a. Accordingly, as is shown in the partially cut away view of FIG. 10, an elongated flexible region 25 can be provided, (shown here as a comparatively short region for ease of illustration), providing serpentine flexing of the device as it is manipulated in a cannula. It is also to be understood that in addition to a flexible serpentine driving rod and handle, the present invention also encompasses designs in which a rigid handle and/or driving rod are hinged, (preferably proximal the rotating burr), to produce flexing of the device about its generally longitudinally extending central axis, thereby also facilitating manipulation of the device.

What is claimed is:

1. An device for bone decortication and osteophyte resection, comprising:

an elongated handle;

a rotatably-mounted driving rod received in said handle;

a burr axially connected to said driving rod; and an eccentric support connected to said burr and projecting outwardly from said elongated handle to a distance greater than a radius of the burr.

2. The device for bone decortication and osteophyte resection as set forth in claim 1, wherein, said burr is dumbbell-shaped, said eccentric support terminates in a collar which is disposed around a narrow portion of said dumbbell-shaped burr.

3. The device for bone decortication and osteophyte resection as set forth in claim 1, further comprising, at least one gripping structure projecting outwardly from the eccentric support.

4. A method of removing bony tissue from a vertebral endplate, comprising, inserting an instrument having a rotatable burr mounted to an elongated handle and an eccentric support projecting outwardly from said elongated handle to a distance greater than a radius of the burr into a patient's intervertebral space;

rotating the instrument to position the eccentric support against a first vertebral surface;

pivoting the instrument about a contact point between the eccentric support and the first vertebral surface such that the rotatable burr is held firmly against a second vertebral surface opposite the first vertebral surface; and rotating the rotatable burr.

5. The method of removing bony tissue from a vertebral endplate as set forth in claim 4, wherein, the instrument is inserted into the patient's intervertebral space through a percutaneously inserted cannula.

6. An improved surgical tool having a handle and a work element which rotates about an axis defined by the handle, wherein the handle provides a support surface for the work element and defines a work region on the work element for engagement against a body surface, wherein the improvement comprises a fulcrum attached to the handle and defining a pivot point disposed on a side of the work element away from the work region.

7. An improved surgical tool as in claim 6, wherein the fulcrum is disposed on a side of the work element opposite to that of the work region.

8. An improved surgical tool as in claim 6, wherein the tool is selected from the group consisting of an osteophyte resector and a vertebral endplate decorticator.

9. An improved surgical tool as in claim 6, wherein the work element rotates about a fixed axis relative to the handle.

10. An improved surgical tool as in claim 6, wherein the handle comprises a straight shaft having an axis which is aligned with the rotational axis of the work element.

* * * * *

UNITED STATES PATENT AND TRADEMARK OFFICE
CERTIFICATE OF CORRECTION

PATENT NO. : 6,030,401
DATED : February 29, 2000
INVENTOR(S) : James F. Marino

It is certified that error appears in the above-indentified patent and that said Letters Patent is hereby corrected as shown below:

Title page, item [54] and col. 1, replace "Endplate" with ENDPLATE--

Signed and Sealed this

Twentieth Day of March, 2001

Attest:

NICHOLAS P. GODICI

Attesting Officer

Acting Director of the United States Patent and Trademark Office